(12) United States Patent
Qiu et al.

(10) Patent No.: US 6,682,538 B2
(45) Date of Patent: Jan. 27, 2004

(54) UMBILICAL CORD CUTTER RETAINER

(76) Inventors: Yiau-Hung Qiu, 235 Chung-Ho Box 8-24, Taipei (TW); Qi-Zhao Guo, 235 Chung-Ho Box 8-24, Taipei (TW)

( * ) Notice: Subject to any disclaimer, the term of this patent is extended or adjusted under 35 U.S.C. 154(b) by 0 days.

(21) Appl. No.: 10/118,197

(22) Filed: Apr. 9, 2002

(65) Prior Publication Data

US 2003/0191477 A1 Oct. 9, 2003

(51) Int. Cl.[7] ............................................. A61B 17/04
(52) U.S. Cl. ...................... 606/120; 606/151; 606/157
(58) Field of Search .......................... 606/120, 151, 606/157, 205, 208

(56) References Cited

U.S. PATENT DOCUMENTS

| | | | | |
|---|---|---|---|---|
| 5,575,796 A | * | 11/1996 | King et al. ................. | 606/120 |
| 5,608,382 A | * | 3/1997 | Webb et al. ................ | 606/120 |
| 5,676,672 A | * | 10/1997 | Watson et al. .............. | 606/120 |
| 5,697,938 A | * | 12/1997 | Jensen et al. ............... | 606/120 |
| 5,797,922 A | * | 8/1998 | Hessel et al. ............... | 606/120 |
| 5,968,054 A | * | 10/1999 | Yeatts et al. ................ | 606/120 |
| 6,421,920 B1 | * | 7/2002 | Jensen ........................ | 606/120 |

* cited by examiner

Primary Examiner—Gary Jackson

(57) ABSTRACT

An umbilical cord cutter retainer comprises a main spanner, a force applying spanner pivotally installed to the main spanner, and a cutting structure inserted in the main spanner. A distal end of the main spanner has an inserting groove for being inserted by a cutting structure. Two front lateral sides of the main spanner have respective umbilical cord clips which have different colors and are detachable. Normally, the umbilical cord clips supports the force applying spanner so as to be expanded from the main spanner. A knife is inserted into the force applying spanner. A knife can be exactly inserted into a place between the two umbilical cord clips for cutting the umbilical cord between the two umbilical cord clips. Moreover, two ends of the inserting groove of the main spanner have guide grooves. Thereby, the cutting structure can be guided into the inserting groove of the main spanner easily.

7 Claims, 4 Drawing Sheets

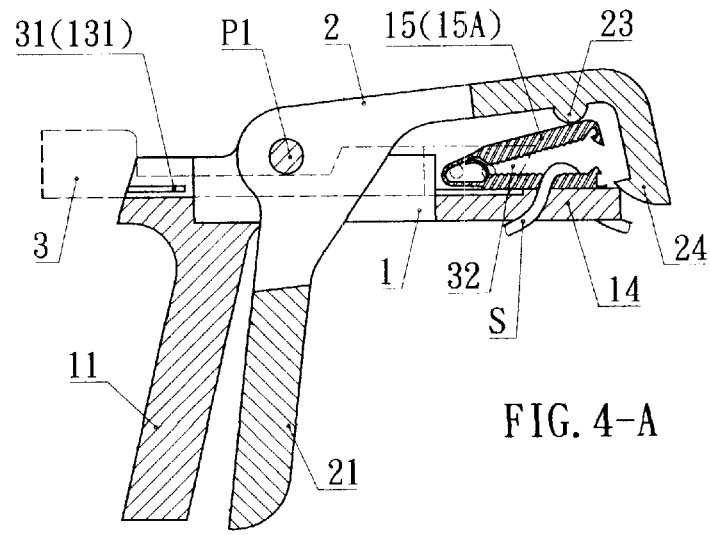
FIG. 4-A
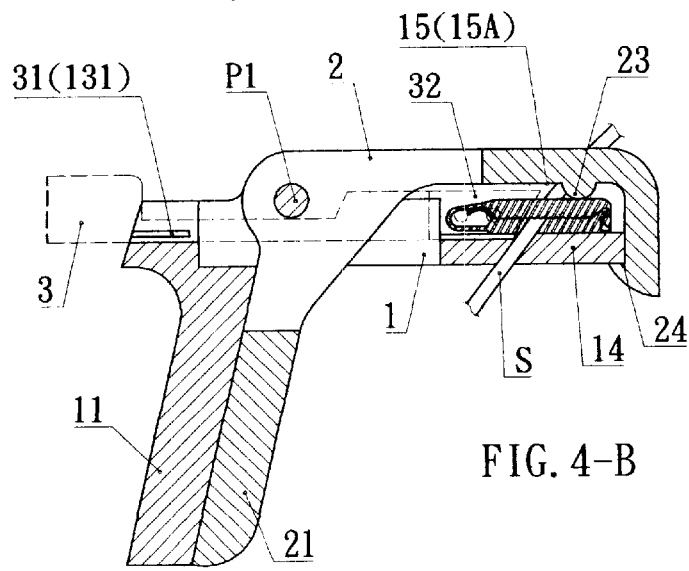
FIG. 4-B
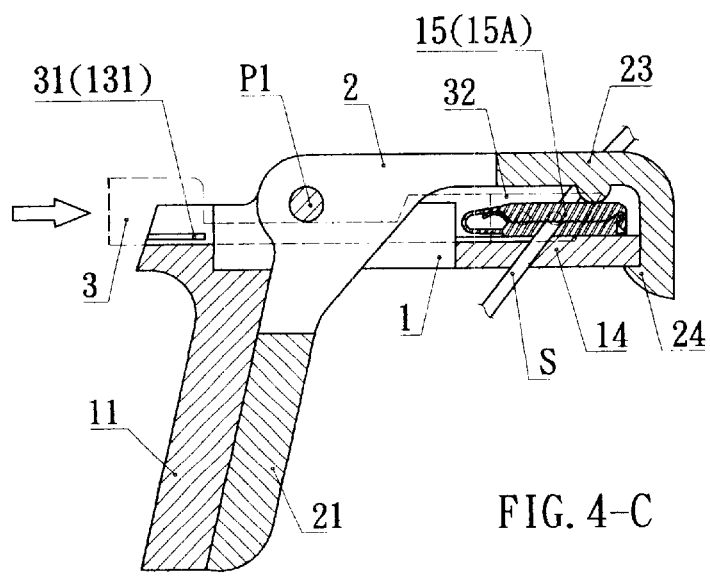
FIG. 4-C

UMBILICAL CORD CUTTER RETAINER

FIELD OF THE INVENTION

The present invention relates to a medical device, and particularly to umbilical cord cutter retainer. Two sides of the umbilical cord are clamped by the umbilical cord clips of the present invention, and thus, the cut umbilical cord will not bleed, an thus it can be cleaned easily.

BACKGROUND OF THE INVENTION

In the prior art, a doctor uses an umbilical cord clip to clamp the umbilical cord of a baby. The structure of a prior art umbilical cord clip is illustrated in FIG. 1. The clip has a saw teeth like clamping end. The upper and lower ends of the foremost of the umbilical cord clip are installed with respective hook portions. When the umbilical cord clip is closed, the hook portions are hooked with one another so as to clamp an umbilical cord tightly. Then the doctor can cut the umbilical cord so that the baby separates from the body of the mother. The defect of this prior art umbilical cord clip is that when an umbilical cord is cut, then it will breed continuously. It is difficult to be cleaned.

SUMMARY OF THE INVENTION

Accordingly, the primary object of the present invention is to provide an umbilical cord cutter retainer comprising a main spanner, a force applying spanner pivotally installed to the main spanner at a proper portion, and a cutting structure inserted in the main spanner.

A handle is downwards extended from a distal end of the main spanner. A solid portion at the distal end of the main spanner is installed with an inserting groove which is communicated to a hollow portion. A foremost of the main spanner is extended with a supporting plate. A retaining hook is installed at a front end of the supporting plate. Two sides of the supporting plate are installed with movable umbilical cord clips. The two umbilical cord clips are opposite at two sides of the supporting plate. A horizontal body of the force applying spanner presses the two umbilical cord clips at two sides of the main spanner downwards. The handle has an engaging hook; and the engaging hook is aligned to the retaining hook of the main spanner;

The cutting structure is inserted to an inserting groove in the main spanner. The inserting groove of the main spanner and then passes through a lower end of the pivotal portion of the main spanner and the force applying spanner. A front end of the cutting structure has a knife and a distal end thereof is installed with a stop edge. The knife resists against the stop edge. The knife protrudes into the two umbilical cord clips of the main spanner for cutting an umbilical cord between the two umbilical cord clips. By the two umbilical cord clips at two sides of an umbilical cord to be cut, a cut umbilical cord will not bleed continuously. Thereby, the clean work can be cleaned easily.

Moreover, two ends of the inserting groove of the main spanner have guide grooves, and the cutting structure has engaging ribs at positions with respect to the guide grooves. Thereby, the cutting structure can be guided into the inserting groove of the main spanner easily.

The various objects and advantages of the present invention will be more readily understood from the following detailed description when read in conjunction with the appended drawing.

BRIEF DESCRIPTION OF THE DRAWINGS

FIG. 4A shows an embodiment about the operation of the present invention.

FIG. 4B shows one embodiment about the clamping operation of the present invention.

FIG. 4C shows one embodiment about the cutting operation of the present invention.

DETAILED DESCRIPTION OF THE PREFERRED EMBODIMENTS

Figure 1:
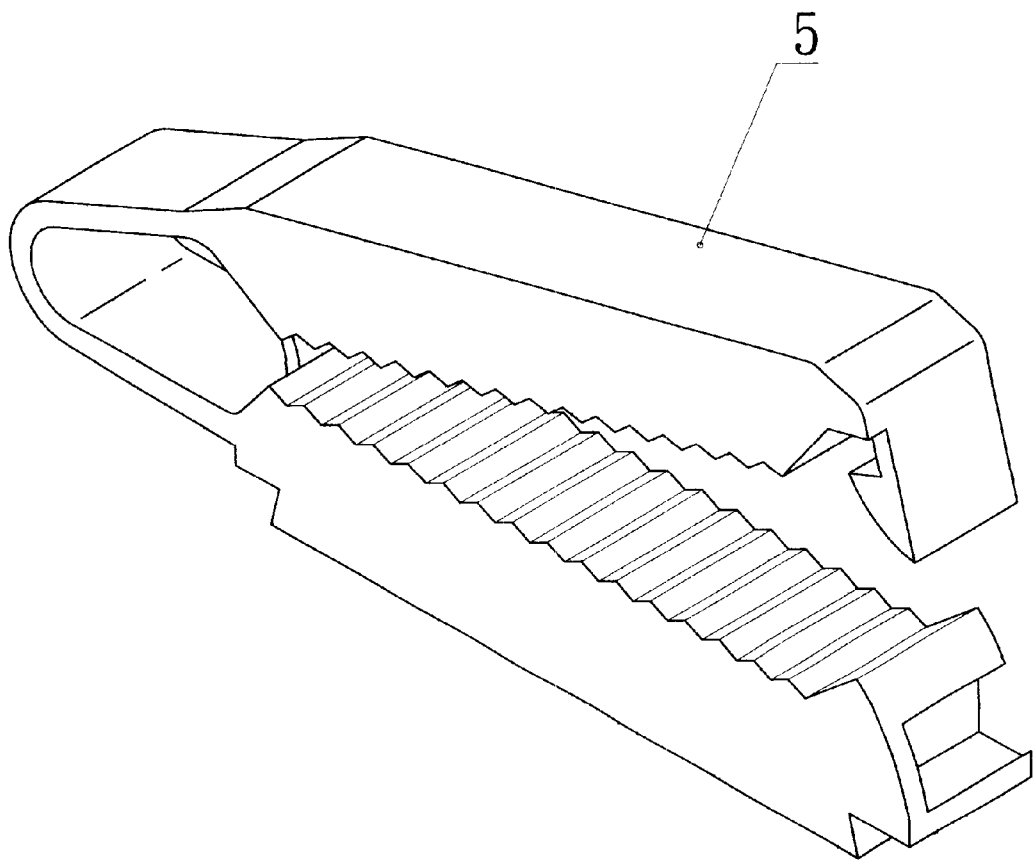
FIG. 1 is a perspective view of the umbilical cord clip of the present invention.
Figure 2:
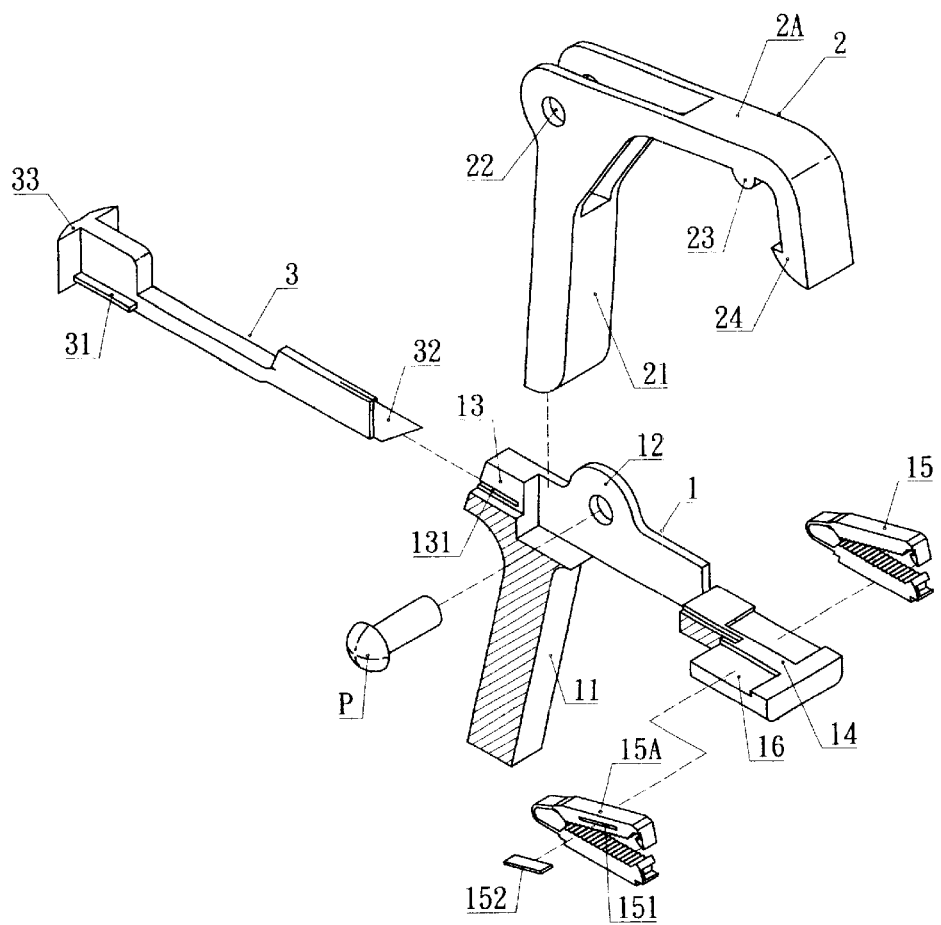
FIG. 2 is an exploded perspective view of the present invention.
Figure 3:
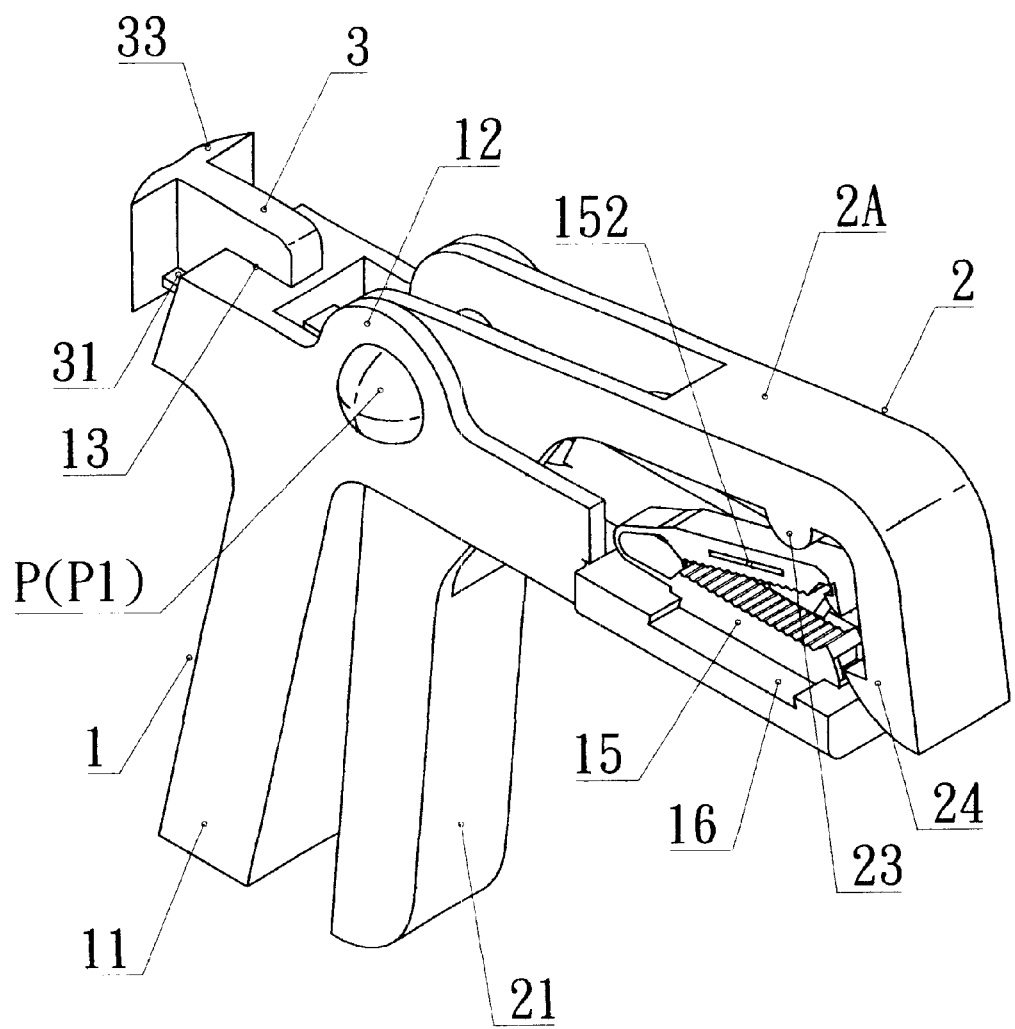
FIG. 3 is an assembled perspective view of the present invention.

With reference to FIGS. 2 and 3, the structure of the present invention is illustrated. The present invention is mainly formed by a main spanner 1, a 10 force applying spanner 2 pivotally installed to the main spanner 1 at a proper portion, and a cutting structure 3 inserted in the main spanner 1.

The main spanner 1 has a solid distal and a hollow middle section. A handle 21 is downwards extended from a distal end of the main spanner 1. A top side of the main spanner 1 has a pivotal piece 12 for installing the force applying spanner 2. The solid portion at the distal end of the main spanner 1 is formed with an inserting groove 13 which is communicated with the hollow portion. Two ends of the inserting groove 13 have respective guide grooves 311 for being inserted by the cutting structure 3. A foremost of the main spanner 1 is extended with a supporting plate 14. A retaining hook 141 is installed at a front end of the supporting plate 14. Two sides of the supporting plate 14 have respective dovetail slots 16. The upper and lower sides of the dovetail slots 16 are installed with movable umbilical cord clips 15 and 15A which are detachable and have different colors. The umbilical cord clips 15 and 15A are opposite at two sides of the supporting plate 14. After the umbilical cord clips 15 and 15A are fixed, each of the umbilical cord clips 15 and 15A has a distance of about 1 cm to the outer edge of the supporting plate 14. Thereby, after the umbilical cord clips 15 and 15A are clamped therein, the clips and the baby has a gap of about 1 cm. Thereby, the measurement work can be performed easily.

A handle 21 is downwards installed from a distal end of the force applying spanner 2. The handle 21 inserts into the hollow portion of the main spanner 1. A pivotal holes 22 are formed on the handle 21 at positions that the force applying spanner 2 is aligned to the pivotal pieces 12. Then, it is pivotally installed with the main spanner 1 through the pin P. Thereby, the horizontal body 2A of the force applying spanner 2 is installed above the supporting plate 14. Moreover, in normal condition, the force applying spanner 2 is supported properly by the umbilical cord clips 15 and 15A at two sides of the force applying spanner 2 and are expanded with respect to the main spanner 1. The bottom end of the force applying spanner 2 has a press 23 which can presses the umbilical cord clips 15 and 15A properly. The portion that the force applying spanner 2 aligns to the retaining hook 141 of the main spanner 1 has an engaging hook 24 corresponding to the retaining hook 141.

The cutting structure 3 is inserted into the inserting groove 13 of the main spanner 1. Thereby, the cutting structure 3 is exactly positioned at a lower end of the pivotal portion Pi of the main spanner 1 and the cutting structure 3. A knife is inserted to a front end of the cutting structure 3. A distal end of the cutting structure 3 has a stop edge 33. When the knife 32 of the stop edge 33 is pushed inwards, the stop edge 33 exactly resists against a distal end of the main spanner 1. At this time, the knife is exactly protruded to be between the two umbilical cord clips 15 and 15A of the main spanner 1 so that an umbilical cord between the two umbilical cord clips 15 and 15A can be cut.

The operation of the present invention is illustrated in FIG. 4. By the pivotal connection of the main spanner 1 and the force applying spanner 2, in normal condition, the two umbilical cord clips 15 and 15A resist against the force applying spanner 2, and thus they are expanded with respect to the main spanner 1 (referring to FIG. 4A).

The umbilical cord cutter retainer is placed between the placenta ad the umbilical cord of a baby. Then umbilical cord cutter retainer applies a force to the handle 21 of the force applying spanner 2 so that the horizontal body 2A of the force applying spanner 2 presses the two umbilical cord clips 15 and 15A at two sides of the main spanner 1 downwards along a fulcrum of the pivotal portion P1. When the engaging book 24 of the force applying spanner 2 is engaged with the retaining hook 141 of the main spanner 1, by tightly clamping the umbilical cord clips 15 and 15A, the umbilical cord S between the placenta and the baby can be pulled out to be in a tight status (referring to FIG. 4B).

When the umbilical cord S is between the two umbilical cord clips 15 and 15A, then the cutting structure 3 is pushed forwards to cause the knife of the cutting structure 3 passes through the tightening placenta S (referring to FIG. 4C). After cutting, the two umbilical cord clips 15 and 15A at two sides of the main spanner 1 are placed on the placenta and the umbilical cord of the baby, which can be identified by colors thereon. After the umbilical cord cutter retainer is used, then it is discarded without being used again.

Since two sides of the umbilical cord are clamped by the umbilical cord clips 15 and 15A, the cut umbilical cord will not bleed, an thus it can be cleaned easily.

A magnetic groove 151 can be installed at a lateral side of the umbilical cord clip 15, a hidden type detector 152 is placed in the magnetic groove 151. When the detector passes through the door of a hospital, an alarm is emitted to avoid the baby to be taken away intentionally or carelessly.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An umbilical cord cutter retainer comprising a main spanner, a force applying spanner pivotally installed to the main spanner, and a cutting means inserted into the main spanner; wherein a first handle is downwards extended from a distal end of the main spanner; the first handle and the main spanner are integrally formed, a solid portion at the distal end of the main spanner is formed with an inserting groove which is communicated to a hollow portion; a foremost of the main spanner is extended with a supporting plate; a retaining hook is installed at a front end of the supporting plate; each of two sides of the supporting plate is installed with a perspective movable umbilical cord clip so that there are two umbilical cord clips; the two umbilical cord clips are oppositely positioned at two sides of the supporting plate;

the force applied spanned is a horizontal body and a second handle integrally extended from the force applied spanner, the force applying spanner presses the two umbilical cord clips at two sides of the main spanner downwards; the force applying spanner has an engaging hook; the engaging hook is aligned to the retaining hook of the main spanner;

a cutting means is inserted into the inserting groove at the distal end of the main spanner 1 and then passes through a lower end of the pivotal portion of the main spanner and the force applying spanner; a front end of the cutting means has a knife and a distal end thereof is installed with a stop edge; the knife resists against the stop edge; the knife protrudes into the two umbilical cord clips of the main spanner for cutting an umbilical cord between the two umbilical cord clips;

wherein by the two umbilical cord clips at two sides of an umbilical cord to be cut, a cut umbilical cord will not bleed continuously, thereby, the clean work can be done easily.

2. The umbilical cord cutter retainer as claimed in claim 1, wherein a distal end of the main spanner is a solid body, and a middle section of the main spanner is a hollow section.

3. The umbilical cord cutter retainer as claimed in claim 1, wherein two ends of the inserting groove of the main spanner have guide grooves; and the cutting means has engaging ribs at positions with respect to the guide grooves, thereby, the cutting means is guided into the inserting groove of the main spanner easily.

4. The umbilical cord cutter retainer as claimed in claim 1, wherein two sides of the supporting plate have respective dovetail slots; the dovetail slots are installed with respective umbilical cord clips which are detachable and have different colors.

5. The umbilical cord cutter retainer as claimed in claim 1, wherein a lower side of the force applying spanner has a press for pressing the umbilical cord.

6. The umbilical cord cutter retainer as claimed in claim 1, wherein a magnetic groove is installed at a lateral side of the umbilical cord clip, a detector is placed in the magnetic groove; when the detector passes through the door of a hospital, an alarm is emitted.

7. The umbilical cord cutter retainer as claimed in claim 1, wherein a fixed umbilical cord clip has a distance of 1 cm to an outer edge of a supporting plate; thereby, a gap is formed between the clip and a baby, so as to achieve the effect of easily measuring.

* * * * *